(12) United States Patent
Woods et al.

(10) Patent No.: US 11,123,334 B2
(45) Date of Patent: Sep. 21, 2021

(54) COMPOSITIONS AND METHODS FOR TREATING OPIOID OVERDOSE AND OPIOID ABUSE

(71) Applicant: Board of Regents of the University of Texas System, Austin, TX (US)

(72) Inventors: James H. Woods, San Antonio, TX (US); Charles Patrick France, San Antonio, TX (US)

(73) Assignee: Board Of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/361,426

(22) Filed: Mar. 22, 2019

(65) Prior Publication Data
US 2019/0290622 A1 Sep. 26, 2019

Related U.S. Application Data

(60) Provisional application No. 62/647,211, filed on Mar. 23, 2018.

(51) Int. Cl.
*A61K 31/439* (2006.01)
*A61P 25/36* (2006.01)

(52) U.S. Cl.
CPC ............ *A61K 31/439* (2013.01); *A61P 25/36* (2018.01)

(58) Field of Classification Search
CPC .................................................. A61K 31/439
See application file for complete search history.

(56) References Cited

PUBLICATIONS

National Institute of Drug Abuse, Naloxone for Opioid Overdose: Life-Saving Science, Mar. 30, 2017, available at https://www.drugabuse.gov/publications/naloxone-opioid-overdose-life-saving-science/naloxone-opioid-overdose-life-saving-science.*

Broadbear et al., Methocinnamox is a potent, long-lasting, and selective antagonist of morphine-mediated antinociception in the mouse: comparison with clocinnamox, beta-funaltrexamine, and beta-chlornaltrexamine, J Pharmacol Exp Ther. Sep. 2000;294(3):933-40.*
Shaw, Dose translation from animal to human studies revisited, The FASEB Journal, vol. 22: 659-661, Mar. 2007.*
U.S. Appl. No. 62/647,211, filed Mar. 23, 2018, James H. Woods.
Broadbear et al, "Methocinnamox Is a Potent, Long-Lasting, and Selective Antagonist of Morphine-Mediated Antinociception in the Mouse: Comparison With Clocin namox, Beta-Funaltrexamine, and Beta-Chlornaltrexamine", J Pharmacol Exp Ther, 294:933-940, 2000.
Gerak, et al., "Self Administration of Cocaine in Monkeys Receiving LAAM Acutely or Chronically", Physiol Behav. Jan. 28, 2008;93(1-2):20-6. Epub Jul. 28, 2007.
Gerak, et al., "Effects of Lorcaserin on Cocaine and Methamphetamine Self-Administration and Reinstatement of Responding Previously Maintained by Cocaine in Rhesus Monkeys", J Pharmacol Exp Ther. Dec. 2016;359(3):383-391. Epub Sep. 20, 2016.
Maguire, et al., "Effects of 1-(2,5-dimethoxy-4-methylphenyl)-2-aminopropane (DOM) and Quipazine on Heroin Self-Administration in Rhesus Monkeys", Psychopharmacology (Berl). Jan. 2013;225(1):173-85. doi: 10.1007/s00213-012-2803-0. Epub Jul. 27, 2012.
Maguire,et al., "Effect of Delay on Self-Administration of Remifentanil Under a Drug Versus Drug Choice Procedure in Rhesus Monkeys", J Pharmacol Exp Ther. Dec. 2013;347(3):557-63. doi:10.1124/jpet.113.208355. Epub Sep. 16, 2013.
Maguire, et al., "Delay Discounting of Food and Remifentanil in Rhesus Monkeys", Psychopharmacology (Berl). Sep. 2013;229(2):323-30. doi: 10.1007/s00213-013-3121-x. Epub May 2, 2013.
Maguire, et al., "Effects of Daily delta-9-tetrahydrocannabinol Treatment on Heroin Self-Administration in Rhesus Monkeys", Behav Pharmacol. Apr. 2016;27(2-3 Spec Issue):249-57.
Maguire, et al., "Effect of Daily Morphine Administration and Its Discontinuation on Delay Discounting of Food in Rhesus Monkeys", Behav Pharmacol. Apr. 2016;27(2-3 Spec Issue):155-64.

* cited by examiner

*Primary Examiner* — Svetlana M Ivanova
(74) *Attorney, Agent, or Firm* — Ballard Spahr LLP (57) ABSTRACT

The disclosure relates to compositions and methods of preventing or treating a subject suffering from opioid toxicity or overdose. The method comprises administering to a patient in need of treatment an effective amount of methocinnamox.

21 Claims, 3 Drawing Sheets

FIG. 5

COMPOSITIONS AND METHODS FOR TREATING OPIOID OVERDOSE AND OPIOID ABUSE

CROSS-REFERENCE TO RELATED APPLICATIONS

This application claims the benefit of the filing date of U.S. Provisional Application No. 62/647,211, filed Mar. 23, 2018. The content of this earlier filed application is hereby incorporated by reference in its entirety.

STATEMENT REGARDING FEDERALLY SPONSORED RESEARCH

This invention was made with government support under grant no. R01DA005018 awarded by the National Institutes of Health. The government has certain rights in the invention.

BACKGROUND

Opioid abuse in the United States is considered an epidemic and its causes are complex, involving many economic, social, medical, biological and other factors. The current opioid epidemic remains a serious public health challenge, despite the availability of medications that are effective in some patients (naltrexone, buprenorphine, and methadone), and attests to the desperate need for more and better approaches to treat this national emergency.

SUMMARY

Disclosed herein are methods of treating opioid toxicity in a subject, the methods comprising: (a) identifying a subject in need of treatment; and (b) administering to the subject a therapeutically effective amount of methocinnamox (MCAM) and a pharmaceutically acceptable salt.

Disclosed herein methods of preventing opioid toxicity in a subject, the methods comprising: (a) identifying a subject in need of treatment; and (b) administering to the subject a therapeutically effective amount of methocinnamox (MCAM) and a pharmaceutically acceptable salt.

Disclosed herein are methods of treating opioid overdose in a subject, the methods comprising: (a) identifying a subject in need of treatment; and (b) administering to the subject a therapeutically effective amount of methocinnamox (MCAM) and a pharmaceutically acceptable salt.

Disclosed herein are methods of preventing opioid overdose in a subject, the methods comprising: (a) identifying a subject in need of treatment; and (b) administering to the subject a therapeutically effective amount of methocinnamox (MCAM) and a pharmaceutically acceptable salt.

Disclosed herein are methods of treating opioid-induced respiratory depression in a subject, the methods comprising: (a) identifying a subject in need of treatment; and (b) administering to the subject a therapeutically effective amount of methocinnamox (MCAM) and a pharmaceutically acceptable salt.

Disclosed herein are methods of preventing opioid-induced respiratory depression in a subject, the methods comprising: (a) identifying a subject in need of treatment; and (b) administering to the subject a therapeutically effective amount of methocinnamox (MCAM) and a pharmaceutically acceptable salt.

Disclosed herein are methods of reversing opioid-induced respiratory depression in a subject, the methods comprising: (a) identifying a subject in need of treatment; and (b) administering to the subject a therapeutically effective amount of methocinnamox (MCAM) and a pharmaceutically acceptable salt.

Disclosed herein are methods of ameliorating one or more signs or symptoms of opioid toxicity or opioid overdose in a subject, the methods comprising: (a) identifying a subject in need of treatment; and (b) administering to the subject a therapeutically effective amount of methocinnamox (MCAM) and a pharmaceutically acceptable salt.

Disclosed herein are methods of preventing or mitigating one or more effects of administration of one or more opioid receptor agonists in a subject in need thereof, the methods comprising administering to the subject a therapeutically effective amount of methocinnamox (MCAM) and a pharmaceutically acceptable salt.

Disclosed herein are methods of reversing or preventing opioid-induced respiratory depression in a subject in need thereof, the methods comprising administering to the subject a therapeutically effective amount of methocinnamox (MCAM) and a pharmaceutically acceptable salt.

Other features and advantages of the present compositions and methods are illustrated in the description below, the drawings, and the claims.

DETAILED DESCRIPTION

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition. The term "patient" includes human and veterinary subjects. In some aspects of the disclosed methods, the "patient" has been diagnosed with a need for treatment for preventing or treating opioid abuse, opioid toxicity or opioid overdose, such as, for example, prior to the administering step.

As used herein, the term "side effect" refers to adverse effects or toxic effects produced by a drug including but not limited to on a tissue or organ system. Such conditions, for example, can include sedation, dizziness, nausea, vomiting, constipation, hyperalgesia, immunologic and hormonal dysfunction, muscle rigidity, myoclonus, bowel dysfunction (e.g., anorexia, gastro-oesophageal reflux, delayed digestion, abdominal pain, bloating) respiratory depression and death.

As used herein, the terms "opioid toxicity" or "opioid overdose" refers to the effects of opioid drugs that are toxic to a subject, resulting in effects that may be mild, moderate or severe including but not limited to respiratory depression or ventilatory depression, hypoxia, loss of consciousness, decreased respiratory rate, decreased respiratory depth, apnea, delirium, hypotension, bradycardia, decreased body temperature, urinary retention, pupil miosis, sedation, dizziness, nausea, vomiting, constipation, hyperalgesia, immunologic and hormonal dysfunction, muscle rigidity, myoclonus, and bowel dysfunction. Opioid toxicity can be assessed by any appropriate method known to a clinical physician or skilled artisan. For example, opioid toxicity can be assessed by performing a central nervous system review by assessing for confusion, altered mental state, excessive drowsiness, lethargy, stupor, slurred speech (new onset), hypoventilation, shortness of breath, apnea, hypoxia, and/or hypercarbia; and/or cardiac review by assessing for bradycardia, hypotension, and/or shock.

The term "overdose" refers to a subject that takes a dose larger than originally intended that results in one or more adverse effects.

As used herein, the term "treating" refers to partially or completely alleviating, ameliorating, relieving, delaying onset of, inhibiting or slowing progression of, reducing severity of, and/or reducing incidence of one or more signs or symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be toxicity, abuse or an overdose relating to the administration of one or more opioids.

As used herein, the phrase "non-dependent" refers to a subject that has or has not taken an opioid at least once and has or has not have become opioid dependent but is not opioid dependent prior to the instance for which treatment is sought.

As used, herein, the phrase "opioid experienced" refers to a subject that has taken an opioid at least once prior to the instance for which treatment is sought. In an aspect, a subject can be opioid experienced and non-dependent suffering from opioid toxicity or opioid overdose. In an aspect, a subject can be opioid experienced and opioid dependent suffering from opioid toxicity or opioid overdose. In an aspect, opioid experienced and non-dependent subjects can be those subjects who have used opioid drugs in the past and have not developed tolerance or dependence to the opioid drugs and can be treated for opioid toxicity or overdose. In an aspect, opioid experienced and opioid-dependent subjects can be those subjects who have used opioid drugs in the past and might have developed tolerance or dependence to the opioid drugs and can be treated for opioid toxicity or overdose.

As used herein, the term "prevent" or "preventing" refers to preventing in whole or in part, or ameliorating or controlling.

Introduction

Described herein are the therapeutic effects of a pseudo-irreversible and highly selective opioid receptor antagonist (methocinnamox; MCAM) for treating opioid abuse and toxicity, and for reversing opioid overdose. MCAM will be compared to the opioid receptor antagonists that are currently used to treat opioid abuse (naltrexone; Vivitrol®) and to reverse opioid agonist-induced respiratory depression (naloxone; Narcan®). Like naltrexone, but unlike buprenorphine (Suboxone®), the antagonist properties of MCAM will block the actions of opioid agonists and the absence of agonist properties will avoid potential adverse interactions with opioid or nonopioid drugs, making it a safe medicine for treating a high-risk population like opioid abusers. Like buprenorphine, but unlike naltrexone and naloxone, MCAM binds in a functionally irreversible manner to opioid receptors, so that its effects are long lasting and not surmounted by large doses of opioid receptor agonists. These pharmacological properties of MCAM make this an effective medication for treating opioid abuse, because of its long duration of action and insurmountability, and also for treating opioid overdose, because of its long duration of protection.

MCAM is a novel opioid receptor antagonist that was developed as a pharmacological tool and it functionally and selectively eliminates μ opioid receptors from in vivo preparations (Broadbear et al, J Pharmacol Exp Ther, 294:933-940, 2000). It was found to be superior to the analogs β-funaltrexamine, β-chlornaltrexamine, and clocinnamox with respect to its in vivo selectivity at μ opioid receptors. Like these analogs and like buprenorphine, it binds to μ opioid receptors in a functionally irreversible manner; it dissociates very slowly and, therefore, is difficult to displace from μ opioid receptors. It prevented any antinociceptive effect of 1000 mg/kg morphine (a 10-fold larger dose than needed for antinociception under control conditions) in the mouse tail-withdrawal assay one hour after administration and continued to show marked antagonism of morphine 48 hours later. Such a long duration of antagonist action may be useful for treating opioid abusers and for reversing and protecting against opioid-induced respiratory depression.

These properties of MCAM were evaluated in nonhuman primates, particularly in comparison with the classical and currently used opioid receptor antagonists naltrexone and naloxone. The assays described herein provide evidence that MCAM is superior to naltrexone in its ability to provide long-lasting, insurmountable blockade of the reinforcing effects of opioid receptor agonists and superior to naloxone in its ability to reverse and protect against respiratory depression produced by opioid receptor agonists. In the case of opioid abuse, MCAM is better than naltrexone in preventing the effects of large doses of opioid receptor agonists and, in particular, the effects of agonists (e.g., fentanyl) that exert behavioral effects when occupying relatively few opioid receptors (low receptor occupancy). Its persistent or long-lived profile of activity makes antagonism by MCAM more difficult to surmount and provides longer antagonist action than currently used opioid receptor antagonists. In overdose situations, a single administration of MCAM can be sufficient to treat (i.e., first reverse then provide long-term protection from re-emergence of respiratory depression or from subsequent administration of an opioid) any opioid-induced toxicity, as compared to the need for repeated administration of the short acting, currently used antidote, naloxone.

Because MCAM has a low affinity for kappa and delta opioid receptors, there is no risk that it will interfere with physiological functions mediated by endogenous opioids acting at these receptors. For example, kappa opioid receptors can mediate pituitary hormone release (e.g., Pfeiffer et al, 1986), and long-term blockade of these receptors by non-selective opioid antagonists is likely to interfere with this action. Moreover, because MCAM has no efficacy at receptors, pharmacodynamic interactions with other nonopioid drugs will not occur. While very effective in some patients, the agonist properties of buprenorphine at μ opioid receptors carry the risk of adverse interactions with other drugs including benzodiazepines and alcohol, both of which are commonly used by opioid abusers as well as former abusers who are in treatment.

MCAM has a novel pharmacological profile. MCAM was designed and found to be different in its binding characteristics and μ opioid receptor binding selectivity. The studies described herein evaluate its potential superiority to naltrexone and naloxone, two opioid receptor antagonists currently available for treating opioid abuse and opioid overdose, respectively. Moreover, because naltrexone and naloxone bind reversibly to opioid receptors, large doses of opioid receptor agonists can surmount their antagonism, and with their relatively short durations of action, repeated administration is often needed to maintain the desired therapeutic (e.g., protective) effect. These characteristics of naltrexone and naloxone are particularly problematic for counteracting the adverse and potentially lethal effects of long-acting opioids such as oxycodone as well as very potent, efficacious agonists such as fentanyl and carfentanil that need to occupy a small fraction of μ opioid receptors to produce behavioral and even toxic effects.

The functional irreversibility and long duration of action of buprenorphine (Kogel et al., 2005) have translated to effective treatment of opioid abuse for some individuals and that effectiveness may be further improved by formulations that are implanted and remain effective for months (Probuphine®). Sustained-release naltrexone is effective for treating opioid abuse in some patients, although it is not well tolerated by all who receive it for this indication, and because naltrexone binds competitively and reversibly to opioid receptors, its antagonist actions can be surmounted by large doses of opioid receptor agonists. By insurmountably blocking the actions of opioid receptor agonists, sustained release (e.g., implantable) MCAM can reduce opioid abuse and provide protection from opioid overdose, while at the same time avoiding pharmacodynamic interactions that can occur even with low efficacy agonists such as buprenorphine (e.g., buprenorphine in combination with benzodiazepines can result in overdose and death). The availability of another safe, effective, and long-acting treatment strategy can be advantageous for many patients (e.g., problems with compliance can be reduced or eliminated by an implantable, pseudo-irreversible antagonist) and in many treatment settings (e.g., rural areas where regular contact with health care and treatment providers is not practical).

As described herein, studies were carried out to compare the acute effects of MCAM with acute effects of naltrexone and naloxone in non-human primate models of opioid toxicity and opioid abuse. The drug toxicity model is opioid-induced respiratory depression and the drug abuse model is opioid self-administration. Naloxone is the comparator drug for respiratory depression studies since it is currently used to treat opioid overdose (Narcan®) and naltrexone is the comparator drug for self-administration studies since it is currently used to treat opioid abuse (Vivitrol®). The respiratory depression assay (Example 1) utilizes a head plethysmograph worn by seated monkeys that permits precise measurement of respiratory rate, and tidal volume with minute volume calculated from those parameters. Opioids, including heroin, fentanyl, and buprenorphine, suppress respiration, buprenorphine to a lesser extent than the opioids with greater efficacy. In the self-administration model (Example 2), monkeys have the opportunity to respond on levers to receive intravenous infusions of heroin or cocaine (Gerak et al, 2008, 2016; Maguire et al, 2012, 2013a,b,c, 2016b). The rationale for using cocaine is to demonstrate the selectivity of the effect, pharmacologically and behaviorally, in terms of blocking the actions of an opioid receptor agonist but not a drug that acts at a different site (e.g., dopamine transporter). In a choice experiment (Example 3) monkeys respond to receive food or drug; this procedure tests for the selectivity of antagonist effects of responding for drug versus food.

The pharmacological profiles of naltrexone and naloxone are very similar and in many respects, these two antagonists are interchangeable; however, because they are used to treat different aspects of opioid abuse, both were studied and compared to MCAM. Naltrexone was studied because it is the opioid receptor antagonist currently used to treat opioid abuse (Vivitrol®); thus, for pretreatment studies MCAM was compared to naltrexone. For pretreatment studies, following administration of an antagonist, the respiratory-depressant effects of heroin were reevaluated every third day until sensitivity to the agonist returns to baseline levels. These studies provide another comparison of the duration of action and surmountability of naltrexone and MCAM. Acute measures of opioid-induced respiratory depression involve administration of a range of doses of heroin alone and then following pretreatment with naltrexone or MCAM. Naloxone (Narcan®) was studied because it is the opioid receptor antagonist currently used to treat opioid overdose; thus, for reversal studies MCAM was compared to naloxone. For reversal studies, a dose of heroin that decreases minute volume ($V_E$) to 75% of control was administered prior to naloxone or MCAM to test for reversibility of established respiratory depression (e.g., related to overdose). The same dose of heroin was administered at specified times thereafter to test for the duration of protection provided by the antagonist.

The ability of each of three doses of naltrexone to modify intravenous self-administration of heroin was determined and the largest dose of naltrexone was also studied with cocaine. Sessions were 2-hr in duration and occur 7 days per week; naltrexone was given before a self-administration session once per week, and its effects on drug self-administration were monitored across days. These data provide information on the duration of action of naltrexone as an antagonist of the reinforcing effects of opioids. The next series of studies were identical except that MCAM was the pretreatment drug. The duration of protection by MCAM against the reinforcing effects of heroin but not of cocaine, and its ability to prevent the reinforcing effects of heroin was established and compared to results with naltrexone.

The studies described herein show that like naltrexone, but unlike buprenorphine (Suboxone®), the antagonist properties of MCAM block the actions of opioid receptor agonists without interacting adversely with non-opioid drugs, making it a safe medicine. Like buprenorphine, but unlike naltrexone and naloxone, MCAM binds in a functionally irreversible manner to µ opioid receptors, such that its effects can be long lasting and not surmounted by large doses of agonists. These studies test proof-of-principle of using a selective, potent, irreversible µ opioid receptor antagonist to reverse opioid-induced respiratory depression and to treat opioid abuse. By insurmountably blocking the actions of opioid receptor agonists and providing protection from opioid overdose, while at the same time avoiding drug/drug interactions that can occur even with low efficacy opioid receptor agonists such as buprenorphine, sustained release (e.g., implantable) MCAM can provide a beneficial approach to treat opioid abuse and overdose. The availability of this effective, long acting, and safe treatment strategy can be advantageous for many patients (e.g., problems with compliance can be reduced or eliminated by an implantable, pseudo-irreversible antagonist) and in many treatment settings (e.g., rural areas where regular contact with health care and treatment providers is not practical).

As described above MCAM is a compound that binds selectively and pseudo-irreversibly to µ opioid receptors where it has antagonist properties. This disclosure describes using this existing compound (MCAM) for treating opioid overdose and opioid abuse. New formulations for each of these indications (overdose and treatment of abuse) are disclosed herein.

MCAM for treating or preventing opioid overdose, toxicity or abuse has several advantages over the currently available treatment options. While naloxone (Narcan) is currently used to treat overdose, it binds reversibly to µ opioid receptors and has a short duration of action; thus, protection of overdose by Narcan is short-lived and can be overcome by re-emergence of the effects of an opioid that has a longer duration of action than naloxone or simply by the administration of large dose of an opioid agonist. In contrast, MCAM binds pseudo-irreversibly and selectively to µ opioid receptors. Because of its pseudo-irreversible binding to opioid receptors, MCAM has a very long duration of action (e.g., 5-7 days) and, at sufficiently large doses, protection of overdose by MCAM will not be surmounted even by large doses of an opioid agonist.

Compositions

As disclosed herein, MCAM can be useful for preventing or treating toxicity or overdose due to the administration of one or more opioid agonists. Currently, the established treatments for preventing or treating toxicity or overdose due to the administration of one or more opioids are not without limitations. MCAM is a selective µ-opioid receptor antagonist that binds in a functionally irreversible manner to the µ-opioid receptor and is without effect at said receptor. In an aspect, MCAM can have affinity for the µ-opioid receptor, but has no efficacy at the µ-opioid receptor. In an aspect, MCAM does not induce any direct effects via the µ-opioid receptor. In an aspect, the µ-opioid receptor can be unaffected by the binding of MCAM to the µ-opioid receptor.

MCAM can be useful in the treatment and/or prevention of opioid overdose or opioid toxicity, the treatment, prevention or reversal of respiratory depression, ameliorating one or more signs or symptoms of opioid toxicity or opioid toxicity, and the prevention or mitigation of one or more effects of one or more opioid receptor agonists, resulting from opioid drugs including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, homologues thereof, analogs thereof and any mixtures thereof.

MCAM can also be useful for the treatment of non-dependent subjects suffering from opioid toxicity or overdose or opioid-induced respiratory depression. In an aspect, those subjects who have used any opioid in the past and have not developed tolerance or dependence to any of the opioid can be treated for opioid toxicity or overdose or opioid-induced respiratory depression. MCAM can also be useful for the treatment of subjects that have not used opioids in the past and are first-time users suffering from opioid toxicity or overdose or opioid-induced respiratory depression. MCAM can also be useful for the treatment of subjects that are experienced opioid users suffering from opioid toxicity or overdose or opioid-induced respiratory depression. MCAM can be useful for the treatment of opioid abuse or protecting or preventing opioid overdose in subjects that can be an experienced opioid user that is not actively using opioids. MCAM can also be useful for the treatment of subjects that are non-dependent but experienced opioid users suffering from opioid toxicity or overdose or opioid-induced respiratory depression. In some aspects, the time period of therapeutic effectiveness of MCAM from a single (or multiple) dose(s) administration can be within minutes. The time period of therapeutic effectiveness of MCAM from a single (or multiple) dose(s) administration can last from about 1 minute to 60 minutes, 1 hour to 24 hours or 1 day to 7 days to over 1 week. In an aspect, a time period of therapeutic effectiveness of MCAM can be between 1 to 5, 5 to 10, 10 to 15, 15 to 20, 20 to 25, 25 to 30, 30 to 35, 35 to 40, 40 to 45, 45 to 50, 50 to 55, 55 to 60 minutes, 1 to 4, 4 to 8, 8 to 12, 12 to 16, 16 to 20, 20 to 24 hours, 1 to 2, 2 to 3, 3 to 4, 4 to 5, 5 to 6, 6 to 7 days, 1 to 2 weeks or longer or any time period in between.

In some aspects, MCAM can be used in combination with other therapeutic drugs used to treats subjects suffering from opioid toxicity, overdose or opioid-induced respiratory depression. For example, in some aspects, MCAM can be administered with other opioid receptor antagonists.

Methods of Treatment

Disclosed herein, are methods of treating opioid toxicity in a subject. Disclosed herein, are methods of preventing opioid toxicity in a subject. Disclosed herein, are methods of treating opioid overdose in a subject. Disclosed herein, are methods of preventing opioid overdose in a subject. Disclosed herein, are methods of treating opioid-induced respiratory depression in a subject. Disclosed herein, are methods of preventing opioid-induced respiratory depression in a subject. Disclosed herein, are methods of ameliorating one or more signs or symptoms of opioid toxicity or opioid overdose in a subject. Disclosed herein, are methods of preventing or mitigating one or more effects of administration of one or more opioid receptor agonists in a subject in need thereof. Disclosed herein, are methods of reversing or preventing opioid-induced respiratory depression in a subject in need thereof. In any of the methods disclosed herein, the methods can comprise identifying a subject in need of treatment. The methods can also include administering to the subject a therapeutically effective amount of MCAM and a pharmaceutically acceptable salt.

In an aspect, MCAM can be administered to a subject via constant delivery of low doses, for example, by a sustained release formulation in a method of preventing opioid toxicity, preventing opioid overdose, preventing opioid-induced respiratory depression or preventing one or more effects of administration of one or more opioid receptor agonists.

In an aspect, MCAM can be administered to a subject via a rapid delivery, for example, by injection or nasal administration, in a method of treating opioid toxicity, treating opioid overdose, treating opioid-induced respiratory depression, treating or ameliorating one or more signs or symptoms of opioid toxicity or opioid overdose or reversing opioid-induced respiratory depression.

In an aspect, a therapeutically effective amount of a pharmaceutical composition comprising MCAM and a pharmaceutically acceptable carrier can be administered to the subject. In an aspect, MCAM can bind to the µ-opioid receptor. In an aspect, the µ-opioid receptor can be unaffected by said binding of MCAM to the µ-opioid receptor. In an aspect, the opioid toxicity or overdose or opioid-induced respiratory depression or one or more effects of administration of one or more opioid receptor agonists results from opioid administration to a non-dependent subject. In an aspect, the subject can be an experienced opioid user. In an aspect, the subject can be a non-dependent, experienced opioid user. In an aspect, the administration of MCAM can reduce one or more signs or symptoms of opioid toxicity or overdose. In an aspect, MCAM can ameliorate one or more signs or symptoms of opioid toxicity or overdose. In an aspect, MCAM can prevent or mitigate one or more effects of administration of one or more opioid receptor agonists. In an aspect, MCAM can prevent or reverse opioid-induced respiratory depression. In an aspect, MCAM can reverse and/or prevent one or more signs or symptoms of opioid toxicity or overdose, and in some cases, all of the symptoms of opioid toxicity or overdose, that are associated with actions at µ-opioid receptors. In an aspect, a therapeutically effective amount of MCAM can produce a long lasting relief from opioid toxicity, opioid overdose, one or more signs or symptoms of opioid toxicity or overdose, opioid-induced respiratory depression, or one or more effects of administration of one or more opioid receptor agonists. In an aspect, the long lasting relief can last at least 7 days or longer. In an aspect, one or more of the symptoms of opioid toxicity or overdose can be reduced over a period of at least 1 to about 60 minutes. In an aspect, one or more of the symptoms of drug toxicity or overdose can be reduced over a period of at least 1 hour, at least 2 hours, at least 3 hours, at least 4 hours, at least 8 hours, at least 12 hours, at least 16 hours, at least 20 hours, at least 24 hours or more. In an aspect, one or more of the symptoms of opioid toxicity or overdose can be reduced over a period of at least 1 to about 24 hours. In an aspect, one or more of the symptoms of drug toxicity or overdose can be reduced over a period of at least 1 day, at least 2 days, at least 3 days, at least 4 days, at least 5 days, at least 6 days, at least 7 days or more. In an aspect, one or more of the symptoms of opioid toxicity or overdose can be reduced over a period of at least 1 to about 7 days. In an aspect, one or more of the symptoms of drug toxicity or overdose can be reduced over a period of at least 1 week, at least 2 weeks or more. In an aspect, one or more of the symptoms of opioid toxicity or overdose can be reduced over a period of at least 1 to about 2 weeks. In an aspect, the one or more signs or symptoms of opioid toxicity or overdose can be sedation, dizziness, nausea, vomiting, confusion, loss of consciousness, constipation, muscle rigidity, miosis, myoclonus, and respiratory depression.

The pharmaceutical compositions described herein can be formulated to include a therapeutically effective amount of MCAM. In an aspect, MCAM can be contained within a pharmaceutical formulation. In an aspect, the pharmaceutical formulation can be a unit dosage formulation. In an aspect, MCAM can be administered on an as-needed basis.

Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to one or more side effects associated with opioid use.

The pharmaceutical compositions described herein can be administered to the subject (e.g., a human patient) in an amount sufficient to delay, reduce, prevent or reverse the onset or duration of opioid toxicity or overdose or respiratory depression in a subject. Accordingly, in some aspects, the patient can be a human patient. In therapeutic applications, compositions can be administered to a subject (e.g., a human patient) already expressing or diagnosed with one or more opioid toxic symptoms in an amount sufficient to at least partially improve a sign or symptom or to inhibit the progression of (and preferably arrest) the symptoms of the condition, its complications, and consequences. An amount adequate to accomplish this is defined as a therapeutically effective amount. A therapeutically effective amount of a pharmaceutical composition can be an amount that achieves a cure or reverses or reduces one or more signs or symptoms of opioid toxicity or opioid overdose, but that outcome is only one among several that can be achieved. As noted, a therapeutically effective amount includes amounts that provide a treatment in which the onset, progression or expression of one or more of the side effects associated with opioid use or toxicity or overdose or opioid-induced respiratory depression is delayed, hindered, or prevented, or the one or more signs or symptoms associated with opioid use or toxicity or overdose or opioid-induced respiratory depression is reduced, ameliorated or reversed. One or more of the symptoms can be less severe. Recovery can be accelerated in an individual who has been treated.

Amounts effective for this use can depend on the severity of the symptoms of opioid toxicity or overdose or respiratory depression and the weight and general state and health of the subject, but generally range from about 0.1-350 mg of an equivalent amount of the MCAM per dose per subject.

The total effective amount of a MCAM as disclosed herein can be administered to a subject as a single dose, either as a bolus or by infusion over a relatively short period of time, or can be administered using a fractionated treatment protocol in which multiple doses are administered over a more prolonged period of time. Alternatively, continuous intravenous infusions and sustained release formulations sufficient to maintain therapeutically effective concentrations in the blood are also within the scope of the present disclosure.

The therapeutically effective amount or dosage of the MCAM used in the methods as disclosed herein applied to mammals (e.g., humans) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of side effects of the opioid agonists), the age and physical characteristics of the subject and other considerations known to those of ordinary skill in the art. Dosages of MCAM can be in the range of 0.001 mg to 5 mg per kilogram of the subject's body weight. In an aspect, the dosage of MCAM can be 1, 10, 100, 200, 300, or 350 mg total. In an aspect, the dosage of MCAM can be 0.001 to 5 mg/kg. In an aspect, MCAM can be administered orally, intravenously, intramuscularly, subcutaneously, or intranasally. The side effects (e.g., respiratory depression) of opioid receptor agonists can be reversed by 0.32 mg/kg MCAM subcutaneously in rhesus monkeys that received heroin (0.1-1.0 mg/kg). In an aspect, a single administration of MCAM can reverse opioid-induced respiratory depression in a subject. In an aspect, a single administration of MCAM can reverse opioid overdose in a subject. In an aspect, a single administration of MCAM can prevent opioid overdose in a subject for one or more days. In an aspect, a single administration of MCAM can prevent respiratory depression in a subject for one or more days. In some aspects, multiple administrations of MCAM can reverse opioid-induced respiratory depression in a subject. In some aspects, multiple administrations of MCAM can reverse opioid overdose in a subject. In some aspects, multiple administrations of MCAM can prevent opioid overdose in a subject for one or more days. In some aspects, multiple administrations of MCAM can prevent respiratory depression in a subject for one or more days. The equivalent range of MCAM doses in humans assuming a body weight of 70 kg can be about 0.001-5 mg/kg total. In an aspect, the therapeutically effective amount of MCAM can be between 0.001-5 mg/kg of body weight or any amount in between. In an aspect, smaller therapeutically effective doses may retain the ability to reverse one or more side effects (e.g., behaviorally disruptive effects) of opioid receptor agonists.

Pharmaceutical Compositions

As disclosed herein, are pharmaceutical compositions, comprising MCAM and a pharmaceutical acceptable carrier described herein. In some aspects, MCAM can be formulated for intravenous administration. In some aspects, MCAM can be formulated for intramuscular administration. In some aspects, MCAM can be formulated for intranasal administration. In some aspects, MCAM can be formulated for sustained release administration. In some aspects, the sustained release formulation can be implantable. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The compositions can be administered directly to a subject. Generally, the compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) may increase the efficiency of delivery.

The compositions can be formulated in various ways for parenteral or nonparenteral administration. Where suitable, oral formulations can take the form of tablets, pills, capsules, or powders, which may be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used. Thus, compositions can be prepared for parenteral administration that includes MCAM dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

Articles of Manufacture

The compositions described herein can be packaged in a suitable container labeled, for example, for use as a therapy to treat or prevent opioid toxicity or opioid overdose or opioid abuse or opioid-induced respiratory depression. Accordingly, packaged products (e.g., sterile containers containing the composition described herein and packaged for storage, shipment, or sale at concentrated or ready-to-use concentrations) and kits, including at least MCAM as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent. Alternatively, the compounds can be provided in a concentrated form with a diluent and instructions for dilution.

EXAMPLES

Example 1

Comparison of the Antagonist Effects of Acute Administration of MCAM and naloxone in a Model of Opioid-Induced Respiratory Depression Rationale. The most significant adverse effect of abused opioids (e.g., heroin) is the suppression of respiration, often resulting in overdose and death. The National Center for Health Statistics, Centers for Disease Control and Prevention, estimates that nearly 35,000 opioid-induced overdose deaths occurred in the US in 2015 and current trends indicate that number continues to increase. The respiratory depressant effects of opioids are rapidly reversed by opioid receptor antagonists and the increasing availability of nasally delivered naloxone (Narcan®) is saving lives and dramatically improving outcomes for opioid overdose. Notwithstanding its value in saving lives, the pharmacological properties of Narcan® limit its effectiveness. Most importantly, like naltrexone, naloxone binds to opioid receptors in a competitive, reversible manner such that it has a relatively short duration of action and its effects can be surmounted by large doses of opioid receptor agonists. Thus, rescue from opioid overdose with Narcan® requires close monitoring since the duration of action of the agonist can exceed the duration of action of naloxone, resulting in the re-emergence of respiration depression and possibly death. Moreover, naloxone does not fully protect against the adverse effects of opioids taken after rescue from overdose since the competitive, reversible antagonist properties of naloxone can be overcome by increasing the dose of opioid agonist. In contrast to these limitations in the effectiveness of naloxone for treating overdose, MCAM binds to opioid receptors in an irreversible manner such that it has a very long duration of action and, at the appropriate dose, its effects are not surmounted even by very large doses of opioid agonists. Thus, MCAM is expected to potently reverse opioid agonist-induced respiratory depression for hours and possibly days and to provide protection from either the re-emergence of respiration depression (from the originally administered agonist) or the development of respiratory depression (from further use of an opioid agonist).

Aim. The study described below assessed the therapeutic potential of MCAM as a treatment for opioid overdose by examining its capacity to attenuate the respiratory-depressant effects of heroin in rhesus monkeys. The procedure for this analysis followed the procedure as reported in published studies (Brandt and France, 2000; France and Woods; 1990, France et al, 1990, 1992, 1994, 1995, 1998; Gerak et al, 1994, 1998a,b; Lelas et al, 1998).

Expected results. It is expected that naloxone, naltrexone, and MCAM will antagonize the respiratory depressant effects of heroin, either shifting the dose-response curve rightward (naltrexone and MCAM) or reversing established respiratory depression by heroin (naloxone and MCAM). Antagonism of heroin by naloxone and naltrexone will be surmounted by larger doses of heroin (these experiments can be conducted in a conservative fashion, increasing dose minimally across different determinations, so as to avoid incurring adverse effects of large doses of heroin that are not reversed by opioid receptor antagonists). Antagonism (prevention) by MCAM will, at some dose, not be surmounted by larger doses of heroin. All three antagonists are also expected to reverse an established respiratory depressant effect of heroin. On days subsequent to their administration, no dose of naloxone or naltrexone will prevent heroin-induced respiratory depression. In contrast to the short-acting surmountable antagonism provided by naloxone, MCAM is expected to rapidly reverse respiratory depression as well as continue blocking and protecting against respiratory depressant effects for many hours and possibly days.

Subjects. Four adult rhesus monkeys were used for the respiration studies (sex of the particular subjects used in these studies was determined by the availability of monkeys at the time the studies began). All monkeys received various opioids in previous studies. Some of the monkeys might have been treated previously with opioids in doses sufficient to produce physical dependence, although none of the monkeys was physically dependent at the beginning of the studies described herein.

Apparatus. During respiration studies, monkeys were seated in chairs (model R001; Primate Products, Miami, Fla.). The chairs were located in commercially available ventilated, sound-attenuating chambers. A Lexan platform was mounted on the top of the chair allowing protrusion of the subject's head. A helmet (Plas-Labs, Lansing, Mich.) was attached to the platform and sealed using a latex neck dam. The helmet was connected to a pneumotachometer that measures changes in airflow. Air was drawn through the helmet using a large animal bias flow supply (Data Sciences International, St. Paul, Minn.) set to a flow rate of 10 l/min using an air flow meter (model 4140F, TSI Inc., Shoreview, Minn.). The pneumotachometer was connected to a carrier signal conditioner card connected to an acquisition module (Model ACQ-770, Data Sciences International) which was connected to a computer running Ponemah software (version 4.01; Data Sciences International).

Dependent variables. The primary dependent variable was minute volume ($V_E$) calculated as the tidal volume ($V_T$) multiplied by the number of breaths per minute (f). Changes in airflow were continuously monitored and recorded and transformed to respiration rate (inspirations per minute, f), tidal volume (milliliters per inspiration, $V_T$), and minute volume (milliliters inspired per minute, $V_E$) by Ponemah software. Measurements were calculated every minute and the last 10 minutes of each 30-imnute cycle. For calculating $ED_{75}$ (i.e., estimated dose to decrease $V_E$ to 75% of control), straight lines were fit to the linear portion of individual dose-effect curves using the following equation (GraphPad Software, San Diego, Calif.): effect=log(dose)*slope+intercept, and $ED_{75}$ values are estimated.

Drugs. Naloxone hydrochloride, naltrexone hydrochloride, and heroin hydrochloride, were obtained from the Drug Supply Program of the National Institute on Drug Abuse and dissolved in sterile saline. MCAM was synthesized. All drugs were administered subcutaneously.

Experimental design. Monkeys (n=4) were seated in chairs located in sound-attenuating, ventilated chambers. A head plethysmograph was placed over the head and sealed with rubber neck dams. Sessions lasted up to 2 hours and were preceded by a 30-minute period when baseline measures of ventilation were collected. Single doses of heroin were administered before sessions in order to determine a dose-response function and to identify doses to reliably decrease $V_E$ to at least 75% of control. Both acute and cumulative dose response functions were constructed for heroin. The cumulative dosing procedure allows for a complete heroin dose-response curve to be determined in a single session. For prevention studies, a single dose of vehicle, naltrexone, or MCAM was administered before determination of a cumulative dose-response function. That dose-response function was re-determined on days subsequent to administration of an antagonist in order to determine duration of antagonist action. As much as possible, the doses of heroin used in the cumulative dose-response determination were adjusted so as to capture a shift to the right in the dose-response function, thereby quantifying the magnitude of antagonism and relative surmountability of antagonism. The acute heroin dose-response function was used to determine the dose used in reversal experiments. The smallest dose of heroin decreasing respiration to at least 75% of control was administered and, once a decrease in $V_E$ to at least 75% of control was observed, a dose of naloxone or MCAM was administered. Duration of protection from respiratory depression was assessed by administering the same dose of heroin on days subsequent to the administration of an antagonist.

Figure 1:
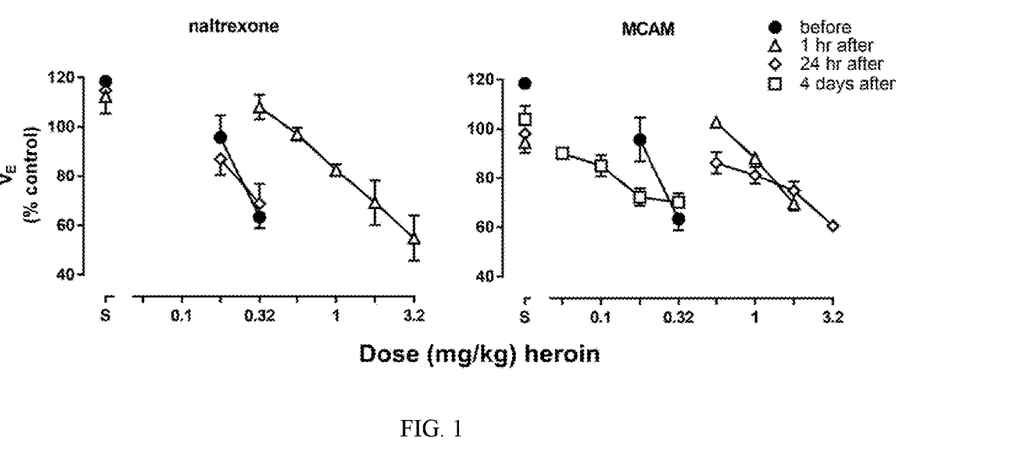
FIG. 1 compares short duration of naltrexone (left panel) and long duration of MCAM (right panel) in preventing heroin-induced respiratory depression.
Figure 2:
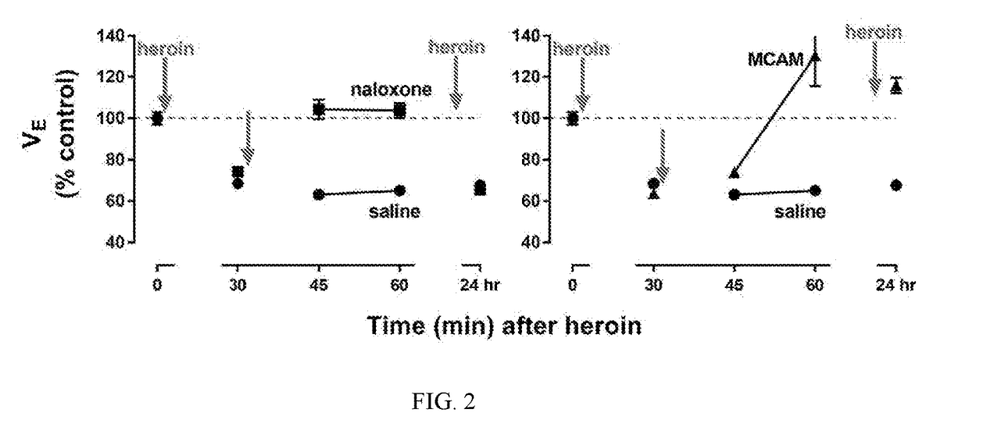
FIG. 2 compares short duration of naloxone (squares, left panel) and long duration of MCAM (triangles, right panel) in reversing and protecting against heroin-induced respiratory depression.

Results. The novel, pseudo-irreversible μ opioid receptor antagonist MCAM attenuates the respiratory-depressant effects of heroin in rhesus monkeys. In monkeys breathing air, heroin dose-dependently decreases respiration to 70% or less of control at the largest dose tested (FIG. 1). On the day of antagonist administration, naltrexone (left panel, FIGS. 1 and 2) and MCAM (right panel, FIGS. 1 and 2) attenuated the respiratory-depressant effects of heroin, shifting the heroin dose-effect curve 6-10 fold rightward. The day after antagonist administration, naltrexone was no longer effective with the heroin dose-response function determined on that day not being different from the control dose-response function (diamonds, left panel, FIG. 1). In contrast, 24 hours after administration, MCAM continued to antagonize the respiratory-depressant effects of heroin (diamonds, right panel, FIG. 1). The respiratory-depressant effects of heroin were not affected 4 days after administration of MCAM (squares, right panel, FIG. 1).

Conclusions. Naltrexone and MCAM attenuated heroin-induced respiratory depression, consistent with their actions as opioid receptor antagonists. The very long lasting effects of MCAM are likely due to its pseudo-irreversible binding to μ opioid receptors. To the extent that MCAM attenuates the respiratory-depressant effects of opioids for prolonged periods, this drug could be superior to currently available treatments for opioid abuse and overdose.

Example 2

Comparison of the Antagonist Effects of Acute Administration of MCAM and naltrexone in a Model of Opioid Abuse (Intravenous Drug Self-Administration)

Rationale. Blockade of reinforcing effects is one current strategy for treating abuse of opioid receptor agonists (e.g., heroin). Naltrexone (Vivitrol®) is the only opioid receptor antagonist that is currently indicated for treating opioid addiction and, while effective in some patients, it has a number of shortcomings that markedly limit its therapeutic use. Naltrexone binds to opioid receptors in a competitive, reversible manner so that its antagonist properties have a short duration of action and the antagonism provided by naltrexone can be surmounted by large doses of opioid agonists. A sustained-release formulation of naltrexone (Vivitrol®; 1-month duration) along with the recent development of a long-acting (6-month) formulation of buprenorphine (Probuphine®) extend the duration of treatment provided by a single administration, which is particularly useful in patients who do not have easy access to health care providers. Unfortunately, the antagonist actions of Vivitrol® are surmounted by large doses of opioid receptor agonists, so that reinforcing effects can be achieved by increasing the dose and protection from relapse to opioid abuse cannot be assured. MCAM combines some of the properties of naltrexone and buprenorphine to provide advantages over these approaches since it binds in a functionally irreversible manner to opioid receptors such that its duration of action is very long, and at appropriate doses, its effects will not be surmounted by even very large doses of opioid receptor agonists; additionally, because it is an antagonist, there will not be pharmacodynamic interactions with nonopioid agonists. Some opioid receptor agonists would not be effective for treating pain in patients being treated with MCAM because of its irreversible, long duration of antagonism; however, larger doses of high efficacy opioid receptor agonists will produce analgesia, nonopioid pain medications (e.g., NSAIDS) will not be affected by MCAM, and after removal of MCAM receptor function and sensitivity to opioids will return within 7-10 days. The experiments described herein compare MCAM to naltrexone for its ability to antagonize the reinforcing effects of opioid receptor agonists on the following dimensions: 1) potency; 2) duration of antagonist action; 3) relatively surmountability of antagonism; and 4) selectivity for antagonizing reinforcing effects of opioids and not cocaine.

Aim. The opioid epidemic remains a serious public health challenge, despite the availability of medications that are effective in some patients (naltrexone, buprenorphine, and methadone); thus, there is a desperate need for more and better approaches to treat this national emergency. This study explores the therapeutic potential of a novel, pseudo-irreversible, and highly selective μ opioid receptor antagonist (MCAM) as a treatment for opioid abuse by examining its capacity to attenuate the reinforcing effects of heroin in rhesus monkeys.

Expected results. At different times, monkeys self-administered either the opioid receptor agonist heroin or cocaine. The antagonist potency, relative duration of action, and relative surmountability of action was compared between MCAM and naltrexone. It is expected that naltrexone will block the reinforcing effects of heroin and not cocaine. Naltrexone is not expected to modify the reinforcing effects of heroin the day after antagonist administration. In contrast, an acute injection of MCAM will potently and insurmountably block the reinforcing effects of opioid receptor agonists for several days without modifying the reinforcing effects of cocaine. Self-administration of heroin is expected to be affected for 5 days or longer after a single administration of MCAM.

Subjects. Five adult rhesus monkeys were used for the self-administration study (sex of the particular subjects used in these studies was determined by the availability of monkeys at the start of the study). All monkeys received various opioids in previous self-administration or other studies. Some of the monkeys might have been treated previously with opioids in doses sufficient to produce physical dependence, although none of the monkeys was physically dependent at the beginning of the studies described herein. Monkeys were instrumented with indwelling venous catheters connected to subcutaneous access ports, according to standard operating procedures (Gerak et al, 2016; Maguire et al, 2012, a,b,c, 2016a,b).

Apparatus. During self-administration studies, monkeys were seated in chairs (model R001; Primate Products, Miami, Fla.). The chairs were located in custom built, ventilated, operant chambers equipped with a response panel containing response levers and stimulus lights. Infusions are delivered by a syringe driver located outside the chamber that is connected to the vascular access port by an intravenous extension set and 20-g Huber needle delivers infusions. Experimental events are monitored and controlled by a PC computer and Med-PC IV software (Med Associates, St. Albans, Vt.).

Dependent variables. The primary dependent variable was the number of responses on the active lever and the number of infusions delivered per unit dose per session.

For calculating $ED_{50}$ (i.e., estimated dose to produce half of the maximum number of drug infusions), straight lines can be fit to the linear portion of individual dose-effect curves using the following equation (GraphPad Software, San Diego, Calif.): effect=log(dose)*slope+intercept, and $ED_{50}$ (self-administration) values can be estimated. Potency ratios can be calculated for each monkey by dividing $ED_{50}$ values obtained in the presence and absence of an antagonist; when 95% CL of the mean dose ratio does not include 1, potency is considered to be significantly altered by treatment. Based on previous results with these procedures, using $\alpha=0.05$ and n=4 provides 80% power to detect an at least 2-fold change in potency. A one-way ANOVA for repeated measures or paired t-tests can be used to compare drug effects across days after a single administration of antagonist. Significance can be set at $p<0.05$.

Drugs. Naltrexone hydrochloride, heroin hydrochloride, and cocaine hydrochloride were obtained from the Drug Supply Program of the National Institute on Drug Abuse and dissolved in sterile saline. MCAM was synthesized. Antagonists were administered subcutaneously; heroin and cocaine were administered intravenously at a rate of 2.3-3.4 ml/minute, delivering volumes of approximately 1 ml/kg body weight.

Experimental design. For the self-administration study, in daily 90-minute sessions and in the presence of a distinctive visual stimulus, monkeys respond to receive intravenous infusions of drug heroin (0.0032 mg/kg/infusion) or cocaine (0.032 mg/kg/infusion) or vehicle under a fixed-ratio 30 schedule of reinforcement. Infusions were followed by a 180-second timeout period when the chamber was dark and responses had no programmed consequence. At different times, monkeys self-administered either the opioid receptor agonist heroin or cocaine. At various times, saline was substituted for drug in order to confirm maintenance of responding by reinforcing effects of agonists.

On different occasions, monkeys received a subcutaneous injection of naltrexone (0.0032-0.032 mg/kg) or MCAM (0.032-0.32 mg/kg) prior to a session when drug was available for self-administration. The pretreatment time was adjusted as needed to capture maximal antagonist activity for each antagonist. Duration of antagonist action was assessed by performance during self-administration sessions on subsequent days. Once effective doses and pretreatment times were identified for naltrexone and MCAM in antagonizing the reinforcing effects of heroin, those doses were studied when monkeys were self-administering cocaine.

Figure 3:
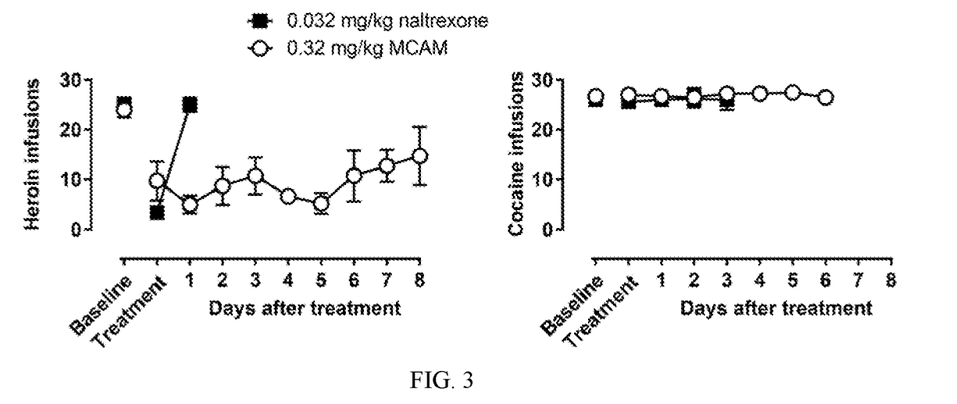
FIG. 3 compares short duration of naltrexone (squares) and long duration of MCAM (circles) in blocking self-administration of heroin (left) and not of cocaine (right).
Figure 4:
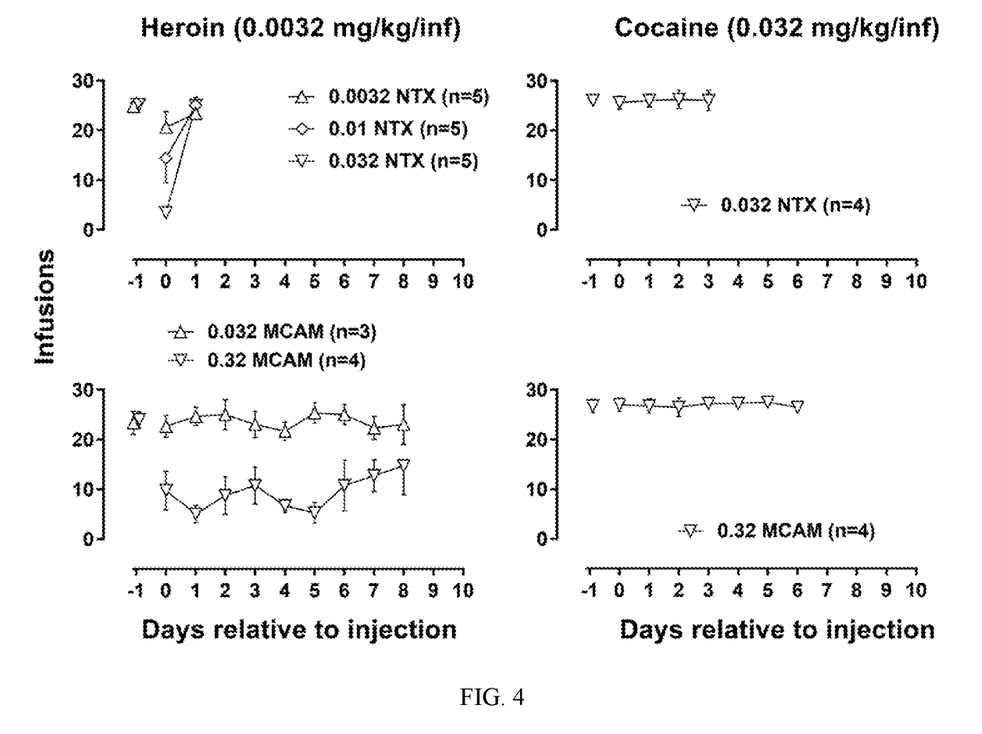
FIG. 4 provides dose-response data from the experiments shown in FIG. 3

Results. The results show sustained decreases in heroin self-administration in rhesus monkeys after a single administration of MCAM. Naltrexone dose-dependently (FIG. 4) decreased responding for heroin during the session immediately following pretreatment, with responding for heroin returning to baseline levels the next day (squares, left panel, FIG. 3; and FIG. 4). MCAM also decreased responding for heroin; responding for heroin remaining decreased for up to 8 days after a single injection of antagonist (FIGS. 3 and 4). Doses of naltrexone (0.032 mg/kg) and MCAM (0.32 mg/kg) that significantly decreased responding for heroin did not affect responding for cocaine (right panel, FIG. 3).

Conclusion. Naltrexone and MCAM decreased heroin but not cocaine self-administration, consistent with their actions as opioid receptor antagonists. The long lasting effect of MCAM on heroin self-administration is likely due to its pseudo-irreversible binding to opioid receptors. To the extent that MCAM selectively attenuates opioid self-administration for prolonged periods, this drug could be superior to currently available treatments for opioid abuse.

Collectively these results show the following: 1) like naltrexone, MCAM decreases responding for heroin, the most widely used and validated laboratory model of opioid abuse; 2) in contrast to the very short duration of action of naltrexone (less than one day), a single injection of MCAM decreases responding for heroin for more than one week; and 3) the effects of naltrexone and MCAM are selective for opioids insofar as neither drug alters responding for cocaine. MCAM, therefore, is effective in blocking the abuse-related effects of heroin for an extended period after a single administration.

Example 3

MCAM Blocks the Reinforcing Effects of the Fentanyl Derivative Remifentanil in Monkeys Choosing Between Food and Drug Infusions Rationale. Effective treatments for opioid abuse should block the reinforcing effects of opioids without generally decreasing behavior. This study compared naltrexone and MCAM in a procedure in which monkeys could choose between receiving a food pellet or an intravenous infusion of the high efficacy fentanyl derivative remifentanil.

Aim. This study explored the therapeutic potential of MCAM in a choice procedure, which can determine whether drugs selectively block reinforcing effects of drugs.

Expected results. It is expected that MCAM will block the reinforcing effects of remifentanil without blocking the reinforcing effects of food, such that monkeys will respond normally for food and not for remifentanil.

Subjects and apparatus. Four adult rhesus monkeys were housed and handled similar to monkeys in Example 2 and the apparatus was identical to that used in Example 2.

Dependent variables. The primary dependent variable was percent choice for drug and for food and the number of reinforcers delivered per component.

Drugs. Naloxone hydrochloride was obtained from the Drug Supply Program of the National Institute on Drug Abuse and dissolved in sterile saline. MCAM was synthesized. Remifentanil hydrochloride was obtained from a commercial source. All drugs were administered intravenously.

Experimental design. In different components of daily sessions, monkeys responded under a fixed ratio 30 schedule to receive a single 300-mg sucrose food pellet or an intravenous infusion of saline or remifentanil. Responses on a second inactive lever were counted but had no programmed consequence. In each of four discrete 30-minute components saline or a different doses of remifentanil was available. Daily sessions comprised four 45-minute cycles; there were a maximum of 10 choices in each cycle for a maximum possible 40 choices per session. A green light in the chamber signaled the availability of food and an infusion. For some sessions, a saline infusion was available during all cycles [not shown]; for other sessions, remifentanil was available during all cycles with the unit dose increasing across cycles (0.032, 0.1, 0.32, and 1.0 µg/kg/infusion).

Results. When the choice was between food and an infusion of saline (data collapsed across the four cycles to a single data point), the monkey shown in FIG. 5 chose food exclusively (circles above "S" in FIG. 5). Similarly, when the choice was between food and a small dose (0.032 or 0.1 µg/kg/infusion) of remifentanil, the monkey chose food exclusively (leftmost data points above "Remifentanil", FIG. 5). In contrast, when the choice was between food and a larger dose (0.32 or 1.0 µg/kg/infusion) of remifentanil, the monkey chose drug exclusively (squares, FIG. 5). When the same experiment was repeated beginning 24 hours after an injection of 1.0 mg/kg MCAM, the monkey chose exclusively food for the next two sessions (days; circles, FIG. 5). Thus, doses of remifentanil that were preferred under control conditions were no longer preferred after administration of MCAM. This monkey chose remifentanil, but only the largest dose, beginning 3 days after receiving MCAM with sensitivity to remifentanil returning to control only 5 days after MCAM.

Figure 5:
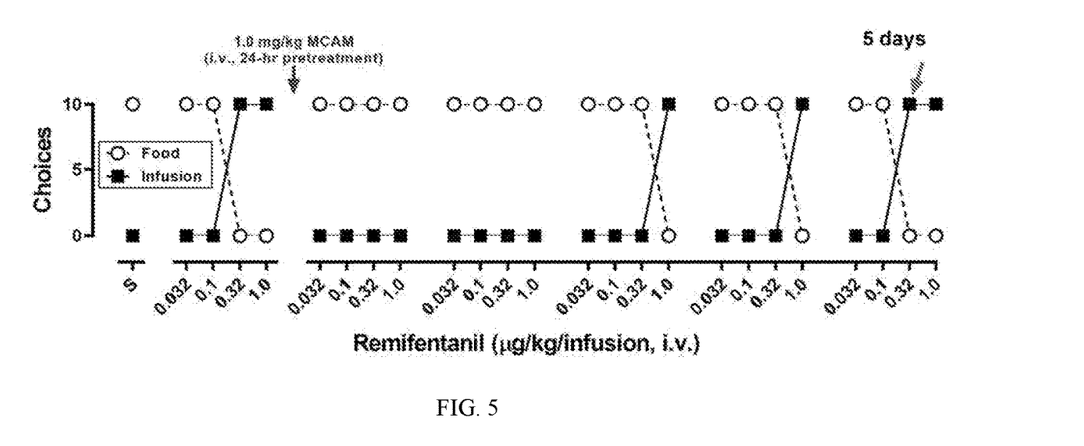
FIG. 5 shows that monkeys choose food (circles) over an infusion (squares) when the infusion is saline or a small dose of remifentanil, but choose remifentanil when the infusion is a larger dose of remifentanil, and that MCAM blocks the choice of remifentanil, with monkeys responding exclusively for food, the next day; sensitivity to remifentanil returns after 5 days from a single injection MCAM.

Conclusion. These data confirm antagonism of the reinforcing effects of opioids by MCAM (in this case remifentanil and in FIG. 3 heroin). Moreover, these data further demonstrate that decreased responding for infusions of an opioid is selective insofar as this monkey continued responding normally for food after administration of MCAM.

What is claimed is:

1. A method of treating a symptom of opioid toxicity or opioid overdose, or opioid-induced respiratory depression in a subject, the method comprising:
   (a) identifying a subject in need of treatment; and
   (b) administering to the subject a therapeutically effective amount of methocinnamox (MCAM) and a pharmaceutically acceptable salt,
   wherein the symptom of opioid toxicity or opioid overdose, or opioid-induced respiratory depression is reduced over a period of at least 24 hours.

2. A method of preventing a symptom of opioid toxicity or opioid overdose, or opioid-induced respiratory depression in a subject, the method comprising:
   (a) identifying a subject in need of treatment; and
   (b) administering to the subject a therapeutically effective amount of methocinnamox (MCAM) and a pharmaceutically acceptable salt,
   wherein the symptom of opioid toxicity or opioid overdose, or opioid-induced respiratory depression is reduced over a period of at least 24 hours.

3. A method of reversing or preventing opioid-induced respiratory depression in a subject in need thereof, the method comprising administering to the subject a therapeutically effective amount of methocinnamox (MCAM) and a pharmaceutically acceptable salt, wherein the opioid-induced respiratory depression is reversed or prevented over a period of at least 24 hours.

4. The method of claim 1, wherein MCAM binds to a μ-opioid receptor and does not induce any direct effects via the μ-opioid receptor.

5. The method of claim 1, wherein the therapeutically effective amount of MCAM is 0.001 to 5 mg/kg.

6. The method of claim 1, wherein MCAM is administered orally, intravenously, intramuscularly, intranasally or transmucosally.

7. The method of claim 1, wherein the opioid toxicity, overdose or opioid-induced respiratory depression results from opioid administration to a non-dependent subject.

8. The method of claim 1, wherein the symptom of opioid toxicity or overdose is reduced over a period of at least 4 days, at least 5 days, at least 6 days or at least 7 days.

9. The method of claim 1, wherein the symptom of opioid toxicity or overdose is sedation, dizziness, nausea, vomiting, constipation, muscle rigidity, myoclonus, or respiratory depression.

10. The method of claim 3, wherein the opioid-induced respiratory depression is reversed or prevented over a period of at least 4 days, at least 5 days, at least 6 days or at least 7 days.

11. The method of claim 3, wherein MCAM is contained within a pharmaceutical formulation.

12. The method of claim 11, wherein the pharmaceutical formulation is a unit dosage formulation.

13. The method of claim 3, wherein MCAM is administered on an as-needed basis.

14. The method of claim 2, wherein MCAM binds to a μ-opioid receptor and does not induce any direct effects via the μ-opioid receptor.

15. The method of claim 3, wherein MCAM binds to a μt-opioid receptor and does not induce any direct effects via the μ-opioid receptor.

16. The method of claim 2, wherein the therapeutically effective amount of MCAM is 0.001 to 5 mg/kg.

17. The method of claim 3, wherein the therapeutically effective amount of MCAM is 0.001 to 5 mg/kg.

18. The method of claim 1, wherein MCAM is administered orally, intravenously, intramuscularly, intranasally or transmucosally.

19. The method of claim 3, wherein MCAM is administered orally, intravenously, intramuscularly, intranasally or transmucosally.

20. The method of claim 2, wherein the symptom of opioid toxicity or overdose is sedation, dizziness, nausea, vomiting, constipation, muscle rigidity, myoclonus, or respiratory depression.

21. The method of claim 2, wherein the symptom of opioid toxicity or overdose is reduced over a period of at least 4 days, at least 5 days, at least 6 days or at least 7 days.

* * * * *